United States Patent
Roberts et al.

(10) Patent No.: US 10,617,778 B2
(45) Date of Patent: Apr. 14, 2020

(54) SELF-STERILIZING PACKAGE AND METHODS FOR MAKING AND USING THE SAME

(71) Applicant: CRYOVAC, INC., Duncan, SC (US)

(72) Inventors: William P. Roberts, Spartanburg, SC (US); Joshua D. Wofford, Simpsonville, SC (US); Charles D. Robnett, Greer, SC (US)

(73) Assignee: Cryovac, Inc., Charlotte, NC (US)

( * ) Notice: Subject to any disclaimer, the term of this patent is extended or adjusted under 35 U.S.C. 154(b) by 241 days.

(21) Appl. No.: 15/523,615

(22) PCT Filed: Oct. 29, 2015

(86) PCT No.: PCT/US2015/057996
§ 371 (c)(1),
(2) Date: May 1, 2017

(87) PCT Pub. No.: WO2016/069864
PCT Pub. Date: May 6, 2016

(65) Prior Publication Data
US 2018/0272019 A1    Sep. 27, 2018

Related U.S. Application Data

(60) Provisional application No. 62/072,481, filed on Oct. 30, 2014.

(51) Int. Cl.
| | |
|---|---|
| *A61L 9/00* | (2006.01) |
| *A62B 7/08* | (2006.01) |
| *B65B 11/58* | (2006.01) |
| *B65B 41/18* | (2006.01) |
| *A61L 2/20* | (2006.01) |

(Continued)

(52) U.S. Cl.
CPC ........ *A61L 2/20* (2013.01); *A61L 2/26* (2013.01); *B65B 7/164* (2013.01); *B65B 55/18* (2013.01); *B65D 81/2076* (2013.01); *B65D 81/28* (2013.01); *A61L 2202/11* (2013.01); *A61L 2202/121* (2013.01); *A61L 2202/16* (2013.01); *A61L 2202/182* (2013.01);
(Continued)

(58) Field of Classification Search
CPC .......... A61L 2/20; B65B 55/02; B29D 22/003
USPC .... 422/1, 5, 28, 120, 123, 305–306; 53/449, 53/170, 202; 428/53, 411.1, 905
See application file for complete search history.

(56) References Cited

U.S. PATENT DOCUMENTS

| | | | | |
|---|---|---|---|---|
| 2006/0039841 A1* | 2/2006 | Rico | ............ | A01N 37/16 422/305 |
| 2006/0178445 A1* | 8/2006 | Mcintyre | ............ | A01N 59/00 523/122 |

FOREIGN PATENT DOCUMENTS

| | | | | |
|---|---|---|---|---|
| WO | WO-2012096739 A1 * | 7/2012 | ............ | A61L 2/26 |

OTHER PUBLICATIONS

PCT International Search Report, dated May 11, 2016.

* cited by examiner

*Primary Examiner* — Monzer R Chorbaji

(57) ABSTRACT

The presently disclosed subject matter provides a system and method for sterilizing a wide variety of products. Specifically, in some embodiments, the presently disclosed subject matter is directed to a package that is capable of self-sterilizing by initiating sterilizing conditions inside the package interior without the necessity of being treated with an externally-supplied sterilizing medium. Particularly, the disclosed package includes at least one dual-layer lid that
(Continued)

comprises inner and outer layers and an interstitial space that houses a sterilizing gas-producing component.

8 Claims, 4 Drawing Sheets

(51) Int. Cl.
   *A61L 2/26* (2006.01)
   *B65B 55/18* (2006.01)
   *B65D 81/20* (2006.01)
   *B65D 81/28* (2006.01)
   *B65B 7/16* (2006.01)
(52) U.S. Cl.
   CPC .. *B65D 2565/387* (2013.01); *B65D 2565/388* (2013.01); *Y02W 30/806* (2015.05)

SELF-STERILIZING PACKAGE AND METHODS FOR MAKING AND USING THE SAME

CROSS-REFERENCE TO RELATED APPLICATIONS

This application claims priority from U.S. Provisional Patent Application No. 62/072,481 filed on Oct. 30, 2014, incorporated herein by reference in its entirety, and further claims priority to PCT/US/15/57996, having an international filing date of Oct. 29, 2015.

FIELD OF THE INVENTION

The presently disclosed subject matter relates generally to self-sterilizing packages that can be used to sterilize a wide variety of products. The presently disclosed subject matter also includes methods of making and using the disclosed packages.

BACKGROUND

The use of a sterilizing gas for retarding, controlling, killing, and/or preventing microbiological contamination of a product is known. Such gases generally include ethylene oxide, chlorine dioxide, sulfur dioxide, nitrogen dioxide, and the like. However, certain sterilizing gases cannot be transported commercially. In these cases, sterilization requires the use of a dedicated facility and equipment to generate the sterilizing gas at the point of use. More generally, sterilization requires large equipment to supply the sterilizing gas to the sterilization process, which takes up space and represents a significant added expense. In addition, controlling the amount of gas generated, the efficiency of the gas production, and the duration of the gas generation has proven difficult and/or unsuccessful using such equipment.

Continuing, sterilizing gases are highly toxic to humans. For example, chlorine dioxide gas can be toxic at vapor concentrations greater than 0.3 parts per million (ppm). As a result, conventional methods of on-site manufacture and delivery of sterilizing gas require not only expensive equipment, but extensive measures for gas containment, facility monitoring, and procedural control to avoid accidental exposure.

Accordingly, there remains a need for a reliable sterilizing system that does not require large and expensive equipment and specialized operators. In addition, there remains a need for a system in which the sterilizing gas is supplied from within a container, avoiding the need for large gas exposure chambers and excessive amounts of sterilization gas. Further, there remains a need in the art for a system that minimizes or eliminates the risk of user exposure to harmful sterilizing gases. Such a system would offer increased mobility, field use, and an increased safety benefit to users.

SUMMARY

In some embodiments, the presently disclosed subject matter is directed to a package comprising an interior and at least one dual-layer wall. Particularly, the dual layer wall comprises an inner permeable layer, an outer impermeable layer, and an interstitial space positioned between the inner and outer layers. The interstitial space comprises a reactant and a co-reactant that combine to produce a sterilizing, sanitizing, or disinfecting gas.

In some embodiments, the presently disclosed subject matter is directed to a method of sterilizing, sanitizing, or disinfecting a product using the disclosed package. Specifically, the method comprises sealing a product into the interior of the package, waiting a desired amount of time to effect sterilization, sanitation, or disinfection, and unsealing the package to access the product.

BRIEF DESCRIPTION OF THE DRAWINGS

FIG. 1b is a cross-sectional view of the package of FIG. 1a.

FIG. 2b is a cross-sectional view of the support member of FIG. 2a.

DETAILED DESCRIPTION

I. General Considerations

The presently disclosed subject matter provides a system and method for sterilizing a wide variety of products, including (but not limited to) medical products. Specifically, in some embodiments, the presently disclosed subject matter is directed to a package that is capable of self-sterilizing by initiating sterilizing conditions inside the package interior without the necessity of being treated with an externally-supplied sterilizing medium. To this end, in some embodiments, the disclosed packages can be formed from one or more barrier materials such that the sterilizing conditions can be maintained within the package for a desired period of time.

Figure 1A:
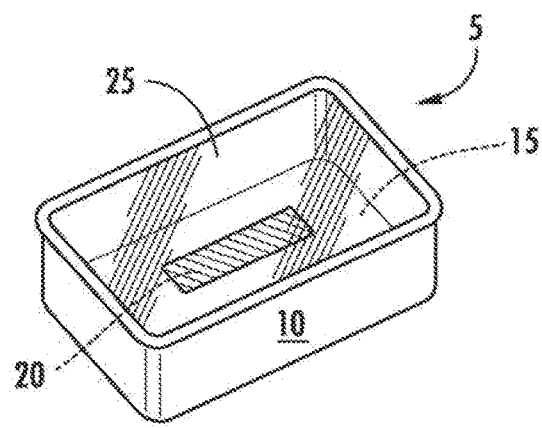
FIG. 1a is a perspective view of one embodiment of a package in accordance with some embodiments of the presently disclosed subject matter.
Figure 1B:
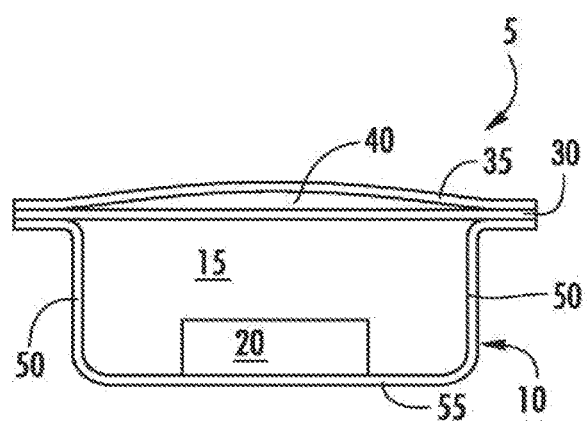

FIGS. 1a and 1b illustrate one embodiment of package 5 that includes product support member 10 comprising cavity 15 for housing product 20. In some embodiments, support member 10 is in the form of a tray having sidewalls 50 and base 55 that define the cavity. Dual lid 25 encloses product 20 within cavity 15 and comprises inner film 30, outer film 35, and interstitial space 40 that houses sterilizing gas-producing component 45. When a sterilizing gas is generated, it migrates through inner film 30 into cavity 15 to sterilize product 20, as set forth in more detail herein below.

II. Definitions

While the following terms are believed to be understood by one of ordinary skill in the art, the following definitions are set forth to facilitate explanation of the presently disclosed subject matter.

Unless defined otherwise, all technical and scientific terms used herein have the same meaning as commonly understood to one of ordinary skill in the art to which the presently disclosed subject matter pertains. Although any methods, devices, and materials similar or equivalent to those described herein can be used in the practice or testing of the presently disclosed subject matter, representative methods, devices, and materials are now described.

Following long-standing patent law convention, the terms "a", "an", and "the" can refer to "one or more" when used in the subject specification, including the claims. Thus, for example, reference to "a package" can include a plurality of such packages, and so forth.

Unless otherwise indicated, all numbers expressing quantities of components, conditions, and so forth used in the specification and claims are to be understood as being modified in all instances by the term "about". Accordingly, unless indicated to the contrary, the numerical parameters set forth in the instant specification and attached claims are approximations that can vary depending upon the desired properties sought to be obtained by the presently disclosed subject matter.

As used herein, the term "about", when referring to a value or to an amount of mass, weight, time, volume, concentration, and/or percentage can encompass variations of, in some embodiments ±20%, in some embodiments ±10%, in some embodiments ±5%, in some embodiments ±1%, in some embodiments ±0.5%, and in some embodiments to ±0.1%, from the specified amount, as such variations are appropriate in the disclosed materials and methods.

As used herein, the term "abuse layer" can refer to an outer film layer and/or an inner film layer, so long as the film layer serves to resist abrasion, puncture, and other potential causes of reduction of package integrity, as well as potential causes of reduction of package appearance quality. Abuse layers can comprise any polymer, so long as the polymer contributes to achieving an integrity goal and/or an appearance goal. In some embodiments, the abuse layer can comprise polyamide, polyolefin, polyester, and/or combinations thereof.

As used herein, the terms "barrier" and/or "barrier layer" can refer to the ability of a film or film layer to serve as a barrier to one or more gases. For example, oxygen barrier layers can comprise, but are not limited to, ethylene/vinyl alcohol copolymer, polyvinyl chloride, polyvinylidene chloride, polyamide, polyester, polyacrylonitrile, and the like, as known to those of ordinary skill in the art. In some embodiments, the barrier film or layer has an oxygen transmission rate of no more than 100 cc $O_2/m^2 \cdot day \cdot atm$; in some embodiments, less than 50 cc $O_2/m^2 \cdot day \cdot atm$; in some embodiments, less than 25 cc $O_2/m^2 \cdot day \cdot atm$; in some embodiments, less than 10 cc $O_2/m^2 \cdot day \cdot atm$; in some embodiments, less than 5 cc $O_2/m^2 \cdot day \cdot atm$; and in some embodiments, less than 1 cc $O_2/m^2 \cdot day \cdot atm$ (tested at 1 mil thick and at 25° C. in accordance with ASTM D3985, herein incorporated by reference in its entirety).

As used herein, the term "bulk layer" can refer to any layer of a film that is present for the purpose of increasing the abuse-resistance, toughness, and/or modulus of a film. In some embodiments, bulk layers can comprise polyolefin, ethylene/alpha-olefin copolymer, ethylene/alpha-olefin copolymer plastomer, low density polyethylene, linear low density polyethylene, and combinations thereof.

As used herein, the term "copolymer" can refer to polymers formed by the polymerization reaction of at least two different monomers. For example, the term "copolymer" can include the copolymerization reaction product of ethylene and an alpha-olefin, such as 1-hexene. However, in some embodiments the term "copolymer" can include, for example, the copolymerization of a mixture of ethylene, propylene, 1-hexene, and 1-octene.

The term "disinfecting" as used herein refers to a process or method that destroys pathogens or other microorganisms, but may not kill bacterial spores.

As used herein, the term "film" can include, but is not limited to, a laminate, sheet, web, coating, and/or the like, that can be used to package a product. The film can be a rigid, semi-rigid, or flexible product. In some embodiments, the disclosed film is produced as a fully coextruded film, i.e., all layers of the film emerging from a single die at the same time. In some embodiments, the film is made using a flat cast film production process or a round cast film production process. Alternatively, the film can be made using a blown film process, double bubble process, triple bubble process, and/or adhesive or extrusion coating lamination in some embodiments. Such methods are well known to those of ordinary skill in the art.

As used herein, the term "heat seal" refers to any seal of a first region of a film surface to a second region of a film surface, wherein the seal is formed by heating the regions to at least their respective seal initiation temperatures. Heat-sealing is the process of joining two or more thermoplastic films or sheets by heating areas in contact with each other to the temperature at which fusion occurs, usually aided by pressure. In some embodiments, heat-sealing can be inclusive of thermal sealing, melt-bead sealing, impulse sealing, dielectric sealing, and/or ultrasonic sealing. The heating can be performed by any one or more of a wide variety of means, such as (but not limited to) a heated bar, hot wire, hot air, infrared radiation, ultrasonic sealing, and the like.

The term "interior" as used herein with regard to a container refers to the actual inside portion of the container into which a product is inserted.

As used herein, the term "multilayer film" can refer to a thermoplastic film having one or more layers formed from polymeric or other materials that are bonded together by any conventional or suitable method, including one or more of the following methods: coextrusion, extrusion coating, lamination, vapor deposition coating, solvent coating, emulsion coating, or suspension coating.

As used herein, the term "package" refers to packaging materials configured around a product being packaged, and can comprise (but is not limited to) bags, pouches, trays, and the like. In some embodiments, the package can comprise a product that is surrounded by a packaging material.

The term "sanitizing" as used herein refers to the process or method of reducing bacteria by at least about 99.9%.

As used herein, the term "seal" can refer to any seal of a first region of a film surface to a second region of a film or substrate surface. In some embodiments, the seal can be formed by heating the regions to at least their respective seal initiation temperatures using a heated bar, hot air, infrared radiation, ultrasonic sealing, and the like. In some embodiments, the seal can be formed by an adhesive. Such adhesives are well known in the packaging art. Alternatively or in addition, in some embodiments, the seal can be formed using a UV or e-beam curable adhesive seal.

As used herein, the terms "seal layer", "sealing layer", "heat seal layer", and/or "sealant layer" refer to an outer film layer or layers involved in heat sealing of the film to itself, another film layer of the same or another film, and/or another product that is not a film. Heat sealing can be performed by any one or more of a wide variety of manners known to those of ordinary skill in art, including using heat seal technique (e.g., melt-bead sealing, thermal sealing, impulse sealing, ultrasonic sealing, hot air, hot wire, infrared radiation, and the like), adhesive sealing, UV-curable adhesive sealing, and the like.

The term "sterilizing" or "sterilized" refers to the process of cleansing so as to destroy and prevent the growth of all forms of viable microorganisms. In some embodiments, sterilizing can refer to a combination of a concentration of sterilizing gas and a time exposure interval that will sterilize a product subjected to the gas within a package. Sterilizing conditions can be provided by a wide range of sterilizing gas concentrations in combination with various time intervals. In general, the higher the concentration of a sterilizing gas, the shorter a corresponding time interval needed to establish sterilizing conditions. Accordingly, the effective amount of a sterilizing gas can vary depending upon the length of exposure of the product to the gas. Other factors that can contribute to (or modify) the sterilization effectiveness of a given amount of sterilization gas include temperature, pressure, relative humidity, lighting, and air circulation. In some embodiments, sterilization involves a greater than 3 log reduction in microorganisms; in some embodiments, greater than 4 log reduction; and in some embodiments, greater than 5 log reduction. Further, when the term "sterilizing" is used herein, the term can include in some embodiments disinfecting and/or sanitizing.

As used herein, the term "sterilizing gas" refers to a gas that effectively destroys, neutralizes, and/or inhibits the growth of pathogenic microorganisms without adversely affecting the product being sterilized. In some embodiments, sterilizing gas includes (but is not limited to) chlorine dioxide, ethylene oxide, sulfur dioxide, nitrogen dioxide, nitric oxide, nitrous oxide, carbon dioxide, hydrogen sulfide, hydrocyanic acid, dichlorine monoxide, ozone, and the like. However, this list is not exhaustive and sterilizing gases suitable for use with the presently disclosed subject matter can include any gas that is capable of sterilizing a product. In some embodiments, the term "sterilizing gas" can also include the wide range of sanitizing and disinfecting gases known in the art.

The term "support member" as used herein refers to a component of a package on or in which a product is disposed. For example, medical products can be disposed into a tray-like support member. A support member can include a cavity into which the product is disposed and a peripheral flange that provides a sealing surface for the attachment of a lid to thereby enclose the product within the cavity.

As used herein, the term "tie layer" can refer to any internal film layer having the primary purpose of adhering two layers to one another. In some embodiments, the tie layers can comprise any nonpolar polymer having a polar group grafted thereon, such that the polymer is capable of covalent bonding to polar polymers such as polyamide and ethylene/vinyl alcohol copolymer. In some embodiments, the tie layers can comprise, but are not limited to, modified polyolefin, modified ethylene/vinyl acetate copolymer, and/or homogeneous ethylene/alpha-olefin copolymer.

All compositional percentages used herein are presented on a "by weight" basis, unless designated otherwise.

III. Package 5

III.A. Generally

Referring to the drawings, a package 5 according to the presently disclosed subject matter is shown. In some embodiments, the disclosed package includes at least one dual-layer lid 25 comprising inner and outer layers 30, 35 and interstitial space 40 housing reactant solution 45. Each component of the disclosed package will be discussed individually in more detail below.

III.B. Support Member 10

Figure 2A:
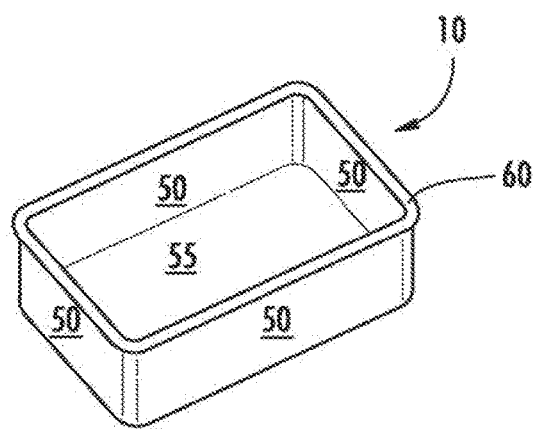
FIG. 2a is a perspective view of one embodiment of a support member in accordance with the presently disclosed subject matter.
Figure 2B:
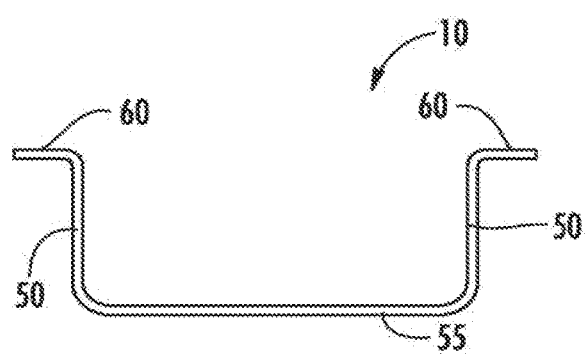

As illustrated in FIGS. 2a and 2b, in some embodiments, package 5 comprises support member 10 which can be in the form of a tray having side walls 50 and base 55 that define a cavity into which a product can be disposed and a headspace that includes the area above and around the packaged product. In some embodiments, flange 60 extends from side walls 50 to provide a sealing surface for attachment of a lid to the support member to enclose product 20 within cavity 15.

Support member 10 can have any desired configuration or shape, e.g., rectangular, round, oval, and the like. Similarly, flange 60 can have any desired shape or design, including a simple, substantially flat design that presents a single sealing surface as shown in the Figures, or a more elaborate design that presents two or more sealing surfaces, as disclosed in U.S. Pat. No. 5,348,752 to Gorlich and U.S. Pat. No. 5,438,132 to Bray et al., the disclosures of which are incorporated by reference herein in their entireties. In some embodiments, flange 60 can include a peripheral lip positioned adjacent and exterior to the sealing surface to facilitate the peelable delamination of lid 25.

The support member can be substantially rigid, semi-rigid, or flexible. For example, the support member can have a 1% secant flex modulus of at least about any of the following values: 120,000; 140,000; 160,000; 180,000; 200,000; 225,000; or 250,000 pounds/square inch (in accordance with ASTM D-790).

Suitable materials from which support member 10 can be formed include (but are not limited to) polyvinylchloride, low density polyethylene, high density polyethylene, polystyrene, polypropylene, polyethylene terephthalate (PET), crystalline polyethylene terephthalate (CPET), amorphous polyethylene terephthalate (APET), polyamides (nylons), polylactic acid (PLA), polyhydroxyalkanoates (PHAs), polycarbonate (PC), polymethyl methacrylate (PMMA), polysiloxanes (silicones), paper pulp, polyurethane, cellulose, acetals, polysulfones, polybutylene terephthalate (PBT), polyimides (PI), polyetherether ketones (PEEK), polyether imides (PEI), polymethylpentene (PMP), styrene-butadiene copolymers, acrylonitrile-butadiene-styrene copolymers, liquid crystal polymers (LCP) and combinations thereof. In some embodiments, any of the materials listed above can include glass fiber, carbon fiber, or any other fiber reinforcement.

In some embodiments, support member 10 can have a substantially gas-impermeable sealant film laminated or otherwise bonded to the inner or outer surface thereof as disclosed in U.S. Pat. Nos. 4,847,148 and 4,935,089, the disclosures of which are hereby incorporated by reference. Alternatively or in addition, in some embodiments, support member 10 can comprise any combination of plastic, paper, glass, aluminum or other metal coatings, and/or coextrusions or laminations of such materials laminated or otherwise bonded to the inner or outer surface thereof. In some embodiments, the materials used to form support member 10 can comprise one or more barrier layers, sealant layers, abuse layers, tie layers, and/or bulk layers. Such layers are well known to those of ordinary skill in the art.

To this end, support member 10 can have oxygen transmission barrier attributes. In these embodiments, support member 10 can have a thickness and composition sufficient to provide an oxygen transmission rate of no more than about any of the following values: 1000, 500, 150, 100, 50, 45, 40, 35, 30, 25, 20, 15, 10, and 5 cubic centimeters (at standard temperature and pressure) per square meter per day per 1 atmosphere of oxygen pressure differential measured at 0% relative humidity and 23° C. (ASTM D-3985).

Support member 10 can have a thickness ranging from about 10 mils to about 25 mils (25.4 to 625 microns). The thickness of side walls 50 can be equal to, greater than, or less than the thickness of base 55.

In some embodiments, support member 10 (and/or lid 25) can comprise an easy open feature. One of ordinary skill in the art would recognize that any of a number of suitable opening mechanisms can be included within the presently disclosed subject matter. For example, ring pull tabs, zippers, and the like can be used. See, for example, U.S. Pat. No. 7,419,301 to Schneider et al.; U.S. Pat. No. 7,395,642 to Plourde et al.; U.S. Pat. No. 7,322,920 to Johnson; U.S. Pat. No. 7,261,468 to Schneider et al.; U.S. Pat. No. 6,539,691 to Beer; U.S. Pat. No. 5,121,997 to La Pierre et al.; U.S. Pat. No. 5,100,246 to La Pierre et al.; U.S. Pat. No. 5,077,064 to Hustad et al.; U.S. Pat. No. 5,022,530 to Zieke; U.S. Pat. No. 6,976,588 to Wischusen et al.; U.S. Pat. No. 5,865,335 to Farrell et al.; U.S. Pat. No. 5,332,150 to Poirier; U.S. Pat. No. 4,778,059 to Martin et al.; and U.S. Pat. No. 4,680,340 to Oreglia et al., the entire disclosures of which are incorporated herein by reference.

Although the support members depicted in the enclosed Figures depict only one compartment to house product 20, it is within the scope of the presently disclosed subject matter that the disclosed package can include support members formed with one or more compartments to house a plurality of products.

It should also be appreciated that the presently disclosed subject matter is not limited to packages comprising rigid or semi-rigid tray support members. Rather, the disclosed subject matter also comprises packages configured as bags, pouches, and the like, with one or more walls or areas with a dual layer as set forth herein.

III.C. Lid 25

Figure 3:
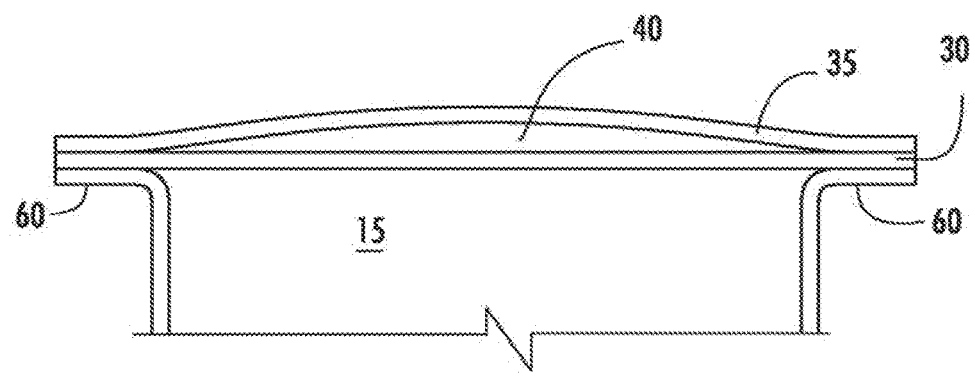
FIG. 3 is an enlarged fragmentary sectional view taken of the lid of a package in accordance with some embodiments of the presently disclosed subject matter.

As shown in FIG. 3, lid 25 comprises inner film 30 and outer film 35, with interstitial space 40 disposed therebetween. Particularly, inner and outer films 30, 35 can be bonded together using any suitable method, such as (but not limited to) adhesive bonding, corona treatment, heat treatment (e.g., heat weld), pressure treatment, and combinations thereof at support member flange 60. Additional films can be included in addition to films 30, 35 as deemed necessary or desired. Interstitial space 40 located between films 30, 35 houses gas-generating component 45 that produces a sterilizing gas. In some embodiments, the dual-layer lid (or dual-layer wall) accounts for at least 5% of the total surface area of package 5.

Inner film 30 is permeable to allow the sterilizing gas produced in the interstitial space to permeate into cavity 15 of the support member to thereby contact product 20. Thus, in some embodiments, inner film 30 has a gas (i.e., oxygen) transmission rate of at least about 10,000 cc/m$^2$/day/atm; in some embodiments, at least about 50,000 cc/m$^2$/day/atm; and in some embodiments, at least about 100,000 cc/m$^2$/day/atm at 73° F., in accordance with ASTM D3985. By another measure of permeability generally associated with porous materials, in some embodiments inner film 30 can have Bendtsen Air Permeability of at least about 10 mL/min.; in some embodiments, at least about 100 mL/min., and in some embodiments, at least about 500 mL/min., in accordance with ISO-5636-3 ($\Delta P$=0.22 atm, area=10 cm$^2$). In some embodiments, inner film 30 does not permit liquids to pass therethrough. Thus, in some embodiments, inner film 30 can have a Hydrostatic Head of at least 1 cm H$_2$O; in some embodiments, at least about 10 cm H$_2$O; and in some embodiments, at least about 100 cm H$_2$O according to AATCC TM 127 (rate of use=60 cm H$_2$O/min.). As a result, separation of package interior 15 and gas-generating component 45 are ensured.

Suitable materials from which inner film 30 can be constructed comprise (but are not limited to) polyethylene or any of a wide variety of ethylene copolymers, including ethylene vinyl acetate, ethylene acrylate copolymers, ethylene acrylic acid copolymers, ethylene alpha-olefin copolymers, spunbonded polyolefin (e.g., Tyvek®), and/or or cellulosic nonwoven films known in the art. Alternatively or in addition, in some embodiments, inner film 30 can be constructed from a film that does not itself have such a high gas permeability, but that has been modified (e.g., by perforation) to be sufficiently permeable to allow a sterilizing gas to pass into support member cavity 15.

Outer film 35 can be impermeable to prevent the sterilizing gas generated in interstitial space 40 from escaping the package and being released into the surrounding environment. Thus, outer film 35 can have a gas (i.e., oxygen) permeability of less than or equal to about 10,000 cc/m$^2$/day/atm; in some embodiments, less than about 1,000 cc/m$^2$/day/atm; in some embodiments, less than about 500 cc/m$^2$/day/atm; and in some embodiments, less than about 10 cc/m$^2$/day/atm at 73° F., in accordance with ASTM D3985. Suitable materials that can be used to construct outer film 35 can include (but are not limited to) ethylene vinyl alcohol (EVOH), polyvinylidene chloride (PVDC), nylon, high density polyethylene (HDPE), and the like.

Interstitial space 40 is positioned between inner and outer films 30, 35 and houses gas-generating component 45. In some embodiments, the gas-generating component comprises reactant 46 and co-reactant 47. Particularly, reactant 46 can in some embodiments be a solution comprising a chlorite or chlorate salt with about 1-40 weight percent sodium chlorite or sodium chlorate. In some embodiments, co-reactant 47 can comprise a water soluble oxidant or acid (such as sodium persulfate, potassium persulfate, acetic acid, citric acid, or hydrochloric acid) which can be in aqueous solution at about 1-40 weight percent concentration. Alternatively or in addition, in some embodiments, co-reactant 47 can be a volatile acid or oxidant (such as acetic acid or nitric oxide) that can be introduced indirectly to reactant 46 as a vapor phase component of the package headspace by gas flushing of the package interior with reactant-containing vapor prior to sealing. It should be understood that reactant 46 and co-reactant 47 are not limited and can include any of the wide variety of materials known in the art that can combine to form a sterilizing gas. Further, reactant and/or co-reactant 46, 47 can in some embodiments include other agents, such as thickeners, gelling agents, stabilizers, pH modifiers, catalysts, co-solvents, surfactants, pH indicators, and the like.

For example, in some embodiments, sterilizing gas (such as chlorine dioxide) can be generated in interstitial space 40 by using a chlorite salt reaction. The generic chemical equation for the chlorate-based reaction is:

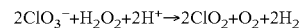

$$2ClO_3^- + H_2O_2 + 2H^+ \rightarrow 2ClO_2 + O_2 + 2H_2O$$

Other reducing agents such as (but not limited to) methanol can be used in place of (or in addition to) peroxide. It should also be noted that reaction temperature has a significant effect on the reaction kinetics. One example of a specific reaction for the disclosed system is:

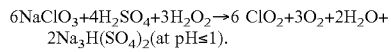
$$6NaClO_3 + 4H_2SO_4 + 3H_2O_2 \rightarrow 6\ ClO_2 + 3O_2 + 2H_2O + 2Na_3H(SO_4)_2 (\text{at pH} \leq 1).$$

In some embodiments, the amount of gas-producing component can be 0.1 to 10 microliters/cm² of dual-layer wall area. In some embodiments, the ratio of package headspace volume to dual-wall area can be 0.1 to 10 cc volume/cm² of dual-layer wall. In some embodiments, reactant 46 has a pH of about 8-13 prior to addition to interstitial space 40.

In some embodiments, film 5 can be an antifog film, i.e., the outer and/or inner layers of films 30, 35 can comprise an antifog and/or surfactant surface treatment or additive to facilitate spreading and adherence of the gas-producing component within interstitial space 40 by reducing the surface tension between at least one film and the reactant solution. Thus, film 5 can incorporate or disperse in effective amounts one or more antifog agents in the film resin before forming the resin into a film or after the film has been formed as a surface treatment. Effective amounts of antifog agent in a film layer can include from about 0.5% to about 12%, from about 1% to about 10%, from about 1.5% to about 8%, and from about 2% to about 6%, based on the total weight of the layer. Suitable antifog agents can include (but are not limited to) polyoxyethylene, sorbitan monostearate, polyoxyethylene sorbitan monolaurate, polyoxyethylene monopalmitate, polyoxyethylene sorbitan tristearate, polyoxyethylene sorbitan trioleate, poly(oxypropylene), polyethoxylated fatty alcohols, polyoxyethylated 4-nonylphenol, polyhydric alcohol, propylene diol, propylene triol, and ethylene diol, monoglyceride esters of vegetable oil or animal fat, mono- and/or diglycerides such as glycerol mono- and dioleate, glyceryl stearate, monophenyl polyethoxylate, and sorbitan monolaurate.

In some embodiments, package 5 can comprise a scavenger composition that scavenges, absorbs, and/or adsorbs sterilizing gas and/or water vapor. Examples of suitable scavengers can include (but are not limited to) phenolic antioxidants (such as Irganox 1076, Irganox 1010), vitamin E, sulfite salt, bisulfite salt, and/or ascorbic/erythorbic acid. In some embodiments, the scavenger can be blended into the walls of support member 10 and/or within the structure of dual lid 25.

In some embodiments, package 5 comprises a moisture scavenger to remove free flowing liquid from the package headspace or interstitial space after or during the sterilization process. Particularly, some sterilizing gas-producing reactions create residual moisture, which can be undesirable, especially in medical applications. To combat this, the disclosed package can comprise a moisture absorbent layer positioned in association with the support member lid. For example, in some embodiments, a moisture absorbent layer can be positioned between the inner and outer lid films (i.e., under outer film 30 and/or above inner film 35). Following sterilization and removal of residual moisture, the absorbent layer can be removed or can remain sealed to the inner or outer film layers 30, 35. Suitable desiccant materials include (but are not limited to) acrylate polymer and calcium oxide inorganics.

In some embodiments, package 5 comprises a moisture scavenger to remove free flowing liquid from the package headspace after or during the sterilization process. Particularly, some sterilizing gas-producing reactions create residual moisture, which can be undesirable. To combat this, the disclosed package can comprise a moisture absorbent layer positioned in association with the lid or support member. For example, in some embodiments, a moisture absorbent layer can be positioned between the inner and outer lid films (i.e., under outer film 30 and/or above inner film 35). Following sterilization and removal of the residual moisture, the absorbent layer can be removed or can remain sealed to inner or outer film layer 30, 35. Suitable desiccant materials include (but not limited to) acrylate polymers and calcium oxide inorganics.

In some embodiments, package 5 comprises an indicator to designate that the package has been successfully sterilized. The indicator can include any substance that produces a visual change in response to exposure to sterilizing gas, water vapor, and/or acid (i.e., a pH indicator). The indicator can be attached, printed, coated, or blended into/onto the package (i.e., support member walls and/or lid). Alternatively or in addition, the indicator can be a separate article, such as a label or tag positioned within the package interior or interstitial space.

IV. Methods of Making Package 5

The presently disclosed package can be constructed by any suitable process known to those of ordinary skill in the art, including (but not limited to) coextrusion, lamination, extrusion coating, and combinations thereof. See, for example, U.S. Pat. No. 6,769,227 to Mumpower, the content of which is herein incorporated by reference in its entirety. For example, in some embodiments, support member 10 can be formed into a desired shape (such as a tray) using thermoforming. Methods of thermoforming sheets to form trays are well known in the art and are therefore not discussed in detail herein.

Once support member 10 has been constructed, product 20 is then placed within cavity 15 of the support member, resting on base 55. Dual lid 25 can then be placed over the product-containing support member and heat sealed to flange 60, thereby creating a perimeter seal and enclosing the product within product cavity 15. The perimeter seal can be formed by applying heat and pressure to the upper surface of dual lid 25 in the areas where the heat-welds are desired to be formed, such as peripherally around flange 60 to completely enclose product 15 within package 5. Any conventional heating element can be used to effect the heat-welds, e.g., a heated metal element having a contact surface that essentially mirrors the shape of, but has a slightly narrower width than, peripheral flange 60. The amount of heat and pressure needed to seal lid 25 to support member 10 is dependent upon a number of factors, e.g., the thickness and composition of the dual lid, and can readily be determined by one having ordinary skill in the art to which the presently disclosed subject matter pertains. It should also be appreciated that the method used to adhere lid 25 to support member 10 is not limited to heat sealing, and any method known in the art can be used, such as the use of adhesives, mechanical closures, ultrasonic welding, and the like. As depicted in the Figures, lid 25 can be hermetically sealed to support member 10 such that package 5 is substantially air and liquid tight.

Figure 4:
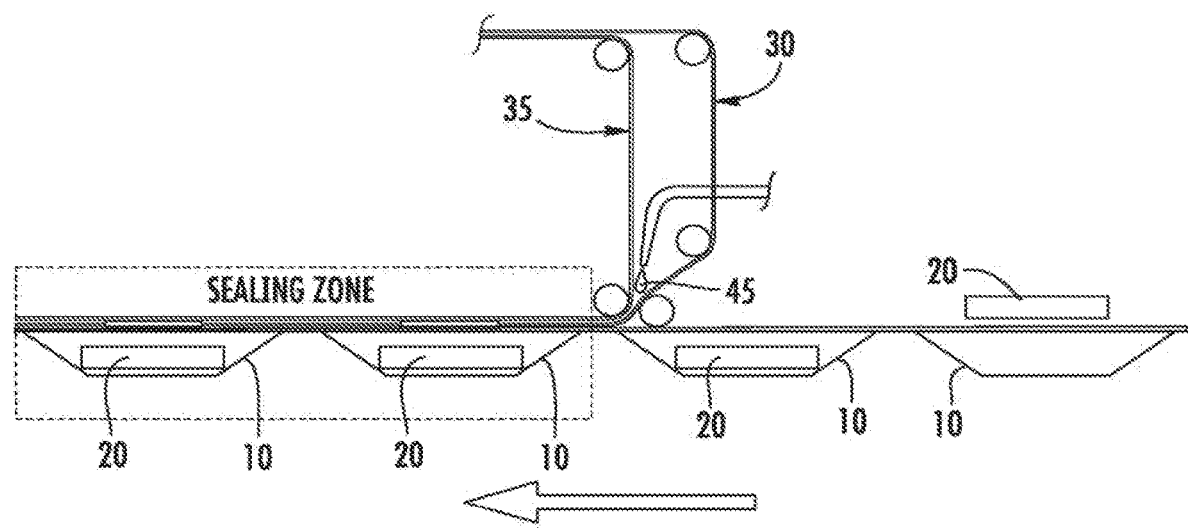
FIG. 4 is a front elevation view of one method of constructing a package in accordance with the presently disclosed subject matter.

As set forth above, sterilizing gas-producing component 45 can be introduced into the interstitial space-facing surfaces of all or part of inner and outer films 30, 35 using any method known in the art, including (but not limited to) spraying, coating, and/or direct liquid dispensing. For example, in some embodiments, a liquid metering nozzle can be used that operates in synchronization with the indexing motion associated with the packaging process, in close proximity to the sealing zone of a packaging machine, as shown in FIG. 4. Before, after, or at the same time reactant 46 is added to interstitial space 40, co-reactant 47 is introduced to the interstitial space by the addition of a separate component that mixes with reactant 46 to form a sterilizing gas before, during, or after sealing of the package (i.e., sealing of films 30, 35 to flange 60).

Thus, a substantially gas-impermeable package for the enclosure of product 20 is formed that provides a sterilizing environment and protects the product from contact with the surrounding environment, including dirt, dust, moisture, microbial contaminants, and the like.

V. Methods of Using Package 5

Figure 5:
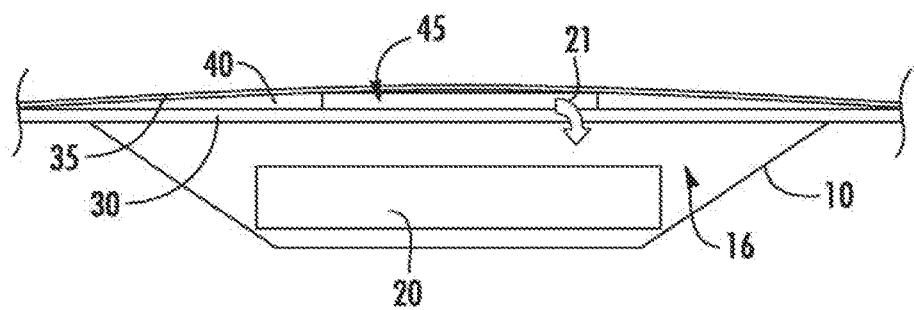
FIG. 5 is a front sectional view of one embodiment of the disclosed package in use.

After the disclosed package has been sealed, the reactant solution undergoes a chemical reaction process, leading to the formation of a sterilizing gas (such as chlorine dioxide gas). The sterilizing gas migrates out of the reactant solution and passes from interstitial space 40, through inner film 30 into package cavity 15 to contact and thereby sterilize product 20, as illustrated by arrow 21 of FIG. 5. In some embodiments, the reaction produces a level of sterilizing gas in the package headspace of about 10 parts per million volume (ppmv) to 10,000 ppmv for a period of about 10 minutes to about 10 days. In some embodiments, the duration and concentration of sterilizing gas is enough to reduce and/or eliminate microorganisms within the package interior. In some embodiments, the package can be held at an elevated temperature (i.e., above room temperature) to accelerate and/or enhance the production of sterilizing gas, enhance the sterilizing gas production, enhance the associated antimicrobial effect, enhance removal of reactive gases/solvents from the package, and/or enhance gas permeation processes.

After a desired amount of time, package 5 can be opened to access sterilized product 20. In some embodiments, the package includes a tab along the package flange region that assists users in peeling the dual lid from the support member.

VI. Advantages of Package 5

The presently disclosed subject matter provides a system and method for the controlled, on-site sterilization of a product. Employing the disclosed package, sterilizing gas can be produced safely, efficiently and economically. Moreover, the disclosed package can minimize or eliminate the release of sterilizing gas at the end of the sterilizing period.

Continuing, the disclosed package assembly is portable and can be configured so that it can be readily moved from place to place. Thus, the package can be assembled and disassembled quickly according to the needs of a particular user.

In addition, the disclosed packages provide an attractive alternative for users who may be unwilling to devote the space or resources required for using a typical autoclave, radiation, or chemical sterilization system, or to bear the extra time delay and cost associated with the use of an outside sterilization service. To this end, the disclosed packages require less space, cost, time, and energy for sterilization compared to large-scale packages and methods currently used in the art.

Further, the products to be sterilized are already within a hermetically sealed package. Accordingly, if a hermetic seal is desired, the disclosed system avoids the need for temporary creation of a breathable wall that an be sealed off after sterilization. As such, the disclosed system requires no post-sterilization handling prior to opening the package, which minimizes the propensity for contamination.

Continuing, by relying on point-of-packaging mixing of reagents that are highly stable and/or freshly prepared from highly stable chemical components, the disclosed method avoids the risk of potential activity loss during distribution and storage associated with pre-manufactured articles such as packaging materials or sachets when they have been pre-loaded with reactant materials at the point of manufacturing. In addition, the disclosed system can be used with high precision and lends itself to interactive control over sterilizing gas generation levels by allowing for incremental adjustments on the packaging line to optimize reactant concentrations and solution (gas) volumes that are added to the interstitial space. Integrity and functionality of the package itself can be assured by adherence to the use of packaging materials and equipment that are commonly used with medical devices, the major change in package design being only the addition of an outer layer of film over the breathable wall of the package. The outer layer can provide an additional source of protection against microbial contamination, gas permeation, abrasion or puncture.

The disclosed package further offers improved safety over traditional packages. Particularly, sterilizing gas production only takes place in isolated small quantities located within the sealed package. Risk of exposure to large quantities of gas is thereby minimized, and the use of excess sterilant gas to surround the package exterior during sterilization is eliminated. Because the disclosed embodiments do not rely on pre-loading of sterilant gas-generating chemicals into packaging materials, shipping, storage, and handling of packaging materials capable of generating sterilizing gas is avoided. Further, any risk of accidental escape of sterilizing gas from packages prior to sealing is minimized by the just-in-time introduction of reactants into the package. In addition, the disclosed package can reduce the amount of harmful or hazardous residuals associated with current sterilization methods, including ethylene oxide sterilization.

As an added safety measure, sensitive sterilant gas monitors can be employed during handling and storage of packages while the internal sterilant gas content is high to ensure that air safety standards are maintained in all packaging areas. In addition, packages that are improperly sealed or have pinholes can be readily identified. As such, the use of the disclosed packages can afford a greater degree of package integrity assurance than can be achieved with conventional sterilization methods that do not provide analogous leak detection.

In addition, the disclosed package is versatile and can be used in accordance with a wide variety of hermetically sealed headspace-containing package types and sizes.

The disclosed package offers a simple and low cost solution to self-sterilize products. Specifically, the disclosed package can be constructed on existing packaging equipment with only minor modifications.

Although several advantages of the disclosed system are set forth in detail herein, the list is by no means limiting. Particularly, one of ordinary skill in the art would recognize that there can be several advantages to the disclosed system that are not included herein.

EXAMPLES

The following Examples provide illustrative embodiments. In light of the present disclosure and the general level of skill, those of ordinary skill in the art will appreciate that the following Examples are intended to be exemplary only and that numerous changes, modifications, and alterations can be employed without departing from the scope of the presently disclosed subject matter.

Sachet Package Test Method

1 Liter dual port bags fitted with 2 septum ports constructed from Nexcel® M312C film (available from Sealed Air Corporation, Duncan, S.C., United States of America) were obtained.

Sachets were prepared by sealing all four sides of a 4 inch×4 inch portion of DuPont Tyvek® 1073B uncoated breathable medical lidding film (available from DuPont Medical Packaging, Wilmington, Del., United States of America) and a 4 inch×4 inch portion of Cryovac LID1051 tray lidding film (available from Cryovac, Inc., Duncan, S.C., United States of America). Prior to heat sealing the fourth side of the sachet, an amount of 10% technical grade sodium chlorite (available from Aldrich Chemical) solution in water was inserted via syringe into the sachet interior (interstitial space).

The sealed sachet was then placed inside a dual-port bag via an open end and oriented with the breathable side facing the package interior. The open end was then sealed in a flattened state, and a headspace gas was introduced through the bag septum via syringe. Where needed, an acetic acid atmosphere was generated by bubbling air through glacial acetic acid in a sparging chamber, filling a source pouch with the gas mixture, and withdrawing with a syringe via septum.

Dual Lid Package Test Method

A series of empty thermoformed packages with Sealed Air ML 2910C 10 mil forming web (available from Sealed Air Corporation, Duncan, S.C., United States of America) and sealant-coated DuPont Tyvek® 2FS lidding film (available from DuPont Medical Packaging, Wilmington, Del., United States of America) on a thermoforming/lidding machine (available from Multivac, Inc., Kansas City, Mo., United States of America). The package lid dimensions were 55 mm×135 mm×25 mm (length×width×depth) for half the packages and 55 mm×135 mm×16 mm (length×width×depth) for the other half of the packages, giving interior volumes of about 150 cc and 100 cc, respectively.

Optionally, one corner of each package was peeled open to insert test packaged items after package preparation.

A second lid of Sealed Air LID1050 antifog lidding material (available from Sealed Air Corporation, Duncan, S.C., United States of America) was added over the Tyvek 2FS lid and 3 edges sealed. Equal volumes of aqueous sodium chlorite solution and aqueous sodium persulfate solutions were added into the space between the two lids via the unsealed edge (using a dual head rotary pump with Digispense 3009 controller, 16.7 microliters per head per cycle, available from IVEK Corporation, North Springfield, Vt., United States of America). The fourth package edge was then immediately heat sealed.

At a predetermined time, a syringe equipped with a needle was used to collect a gas sample from the package interior for colorimetric $ClO_2$ analysis (as described in the examples below). The sampling was performed only once per package.

Optionally, the package was then opened and the contents removed from the package interior.

Chlorine Dioxide Test Method

Analysis of the atmosphere inside the package was performed using an adaptation of the N, N-diethyl-p-phenylenediamine (DPP) chlorine dioxide colorimetric test method (using an Oakton C1032 Colorimeter, available from Oaken Instruments, Vernon Hills, Ill., United States of America). A 10 cc gas sample from the test package was withdrawn via the septum using a syringe that was pre-loaded with 10 mL DPP test solution prepared in either deionized water or a 0.1M phosphate citrate buffer at pH 6.5-6.8 (ensuring neutral pH in the test solution despite the presence of acetic acid vapor in some gas samples). The syringe was then shaken for about 10 seconds to dissolve and react the chlorine dioxide, and transferred to a colorimetric test vial. The reading on the colorimeter was multiplied by a factor of 359 to convert from ppm $ClO_2$ in solution to ppmv $ClO_2$ at standard temperature and pressure in the sample gas.

Microbial Test Method

Evaluation of antimicrobial performance was performed using biological indicator chlorine dioxide test trips (product # ACD/6, *B. atrophaeus* spores, $3.5 \times 10^6$ per strip, available from Mesa Labs, Lakewood, Colo., United States of America) preconditioned at 23° C. and 50% relative humidity for at least 48 hours. At least one test strip was placed in a test package for a period of time, then removed and analyzed for sterility and/or viable organism count according to Mesa Labs published procedures.

Example 1

Chlorine Dioxide Headspace Analysis of Package 1

Figure 6:
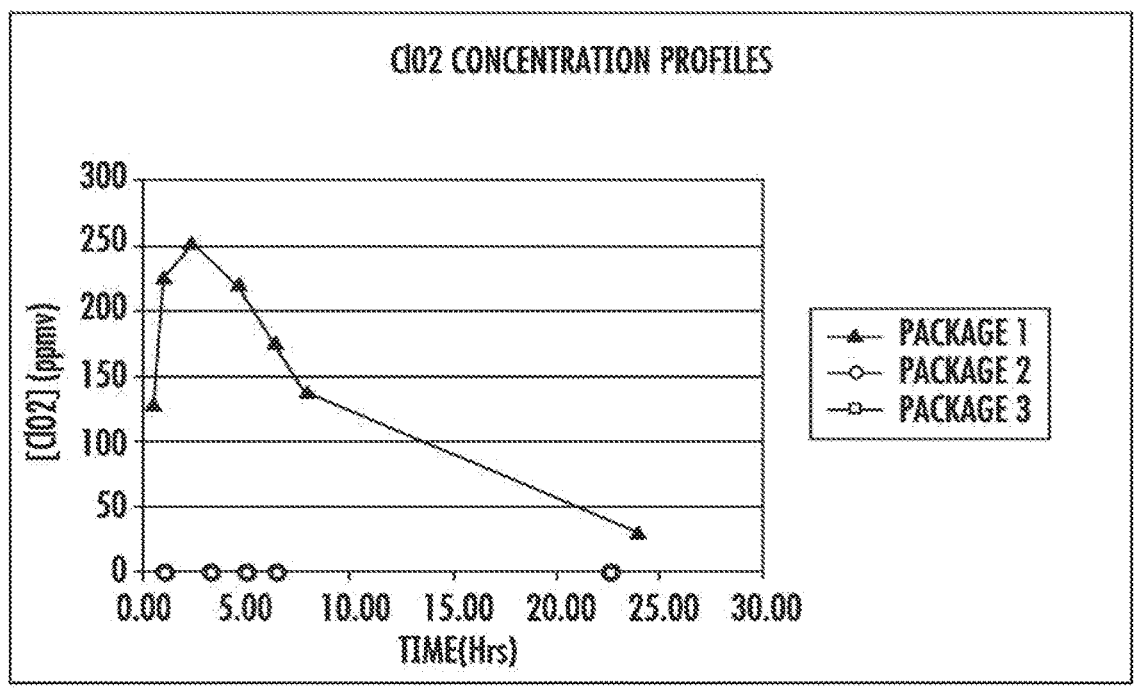
FIG. 6 is a line graph illustrating the chlorine dioxide concentration profile of Packages 1-3 over 25 hours.

Package 1 was prepared according to the sachet package test method set forth above, with 60 microliters of sodium chlorite solution in the sachet and an atmosphere of 300 cc of acetic acid-containing air. The chlorine dioxide level was monitored over a 24 hour period, and the results are shown in Table 1 and FIG. 6. As shown, Package 1 contained a chlorine dioxide level of over 200 ppmv for approximately 4 hours, with a peak level of about 250 ppmv.

Example 2

Chlorine Dioxide Headspace Analysis of Package 2

Package 2 was prepared according to the sachet package test method set forth above, with 60 microliters of sodium chlorite solution in the sachet and an atmosphere of 300 cc ambient air. The chlorine dioxide level was monitored over a 24 hour period, and the results are shown in Table 1 and FIG. 6. As shown, Package 2 did not contain any chlorine dioxide (within experimental error of about 10 ppmv), which demonstrates the necessity of the acidic headspace gas for chlorine dioxide production from the sodium chlorite solution.

Example 3

Chlorine Dioxide Headspace Analysis of Package 3

Package 3 was prepared according to the sachet package test method set forth above, with 60 microliters of sodium chlorite solution in the sachet and an atmosphere of 300 cc of 100% carbon dioxide. The chlorine dioxide level was monitored over a 24 hour period, and the results are shown in Table 1 and FIG. 6. As shown, Package 3 did not contain any chlorine dioxide (within experimental error of about 10 ppmv), which demonstrates that carbon dioxide headspace is not sufficiently acidic (by way of carbonic acid that can form in aqueous solution) under the test conditions for production of chlorine dioxide from the sodium chlorite test solution.

TABLE 1

Chlorine Dioxide Headspace Analysis of Packages 1-3

| Time After MAP Gas Introduction (hours) | Example 1 - [ClO$_2$] in Headspace (ppmv) | Example 2 - [ClO$_2$] in Headspace (ppmv) | Example 3 - [ClO$_2$] in Headspace (ppmv) |
|---|---|---|---|
| 0.5 | 129 | — | — |
| 1.0 | 226 | <10 | <10 |
| 2.3 | 251 | — | — |
| 3.2 | — | <10 | <10 |
| 4.5 | 219 | — | — |
| 4.9 | — | <10 | <10 |
| 6.3 | 176 | — | — |
| 6.4 | — | <10 | <10 |
| 7.8 | 136 | — | — |
| 22.6 | — | <10 | <10 |
| 23.9 | 29 | — | — |

Example 4

Chlorine Dioxide Headspace Analysis Using Acetic Acid as Co-Reactant

A reverse gas-liquid titration was performed against 0.01N potassium hydroxide to determine the volume of acetic acid in the acetic acid-air mixture of Example 1. The resulting concentration determination was 15,000+/−1,000 ppmv acetic acid, in agreement with a saturation level calculation based on the equilibrium vapor pressure of acetic acid.

To test whether the total volume of acetic acid-saturated air was limiting for the production of chlorine dioxide, two test packages (Packages 4 and 5) were prepared as in Example 1, with 60 microliters of sodium chlorite solution in the sachet and an atmosphere of acetic acid-saturated air, varying the headspace volume as shown in Table 2. The chlorine dioxide level was monitored over a 4 hour period, as shown in Table 2. As can be seen, the package with the lower headspace volume (Package 5) contained less chlorine dioxide. The total micromoles of chlorine dioxide present in the headspace are shown alongside the ppmv value to better illustrate the effect of a reduction in headspace volume.

The results indicate that the total amount of acetic acid present is a limiting factor on the amount of chlorine dioxide produced, indicating that packages having a low headspace volume may not achieve sufficiently high levels of chlorine dioxide for sterilization by this method.

TABLE 2

Chlorine Dioxide Headspace Analysis Results of Packages 4-5

| Time After MAP Gas Introduction (hours) | Package 4 (ClO$_2$ Production with 300 cc Initial Headspace Volume) | | Package 5 (ClO$_2$ Production with 150 cc Initial Headspace Volume) | |
|---|---|---|---|---|
| | ppmv | Micromoles | ppmv | Micromoles |
| 1.1 | 258 | 3.45 | 190 | 1.27 |
| 1.7 | 294 | 3.93 | 190 | 1.27 |
| 3.5 | 273 | 3.65 | 197 | 1.32 |

Example 5

Chlorine Dioxide Headspace Analysis Using Citric Acid as Co-Reactant

Figure 7:
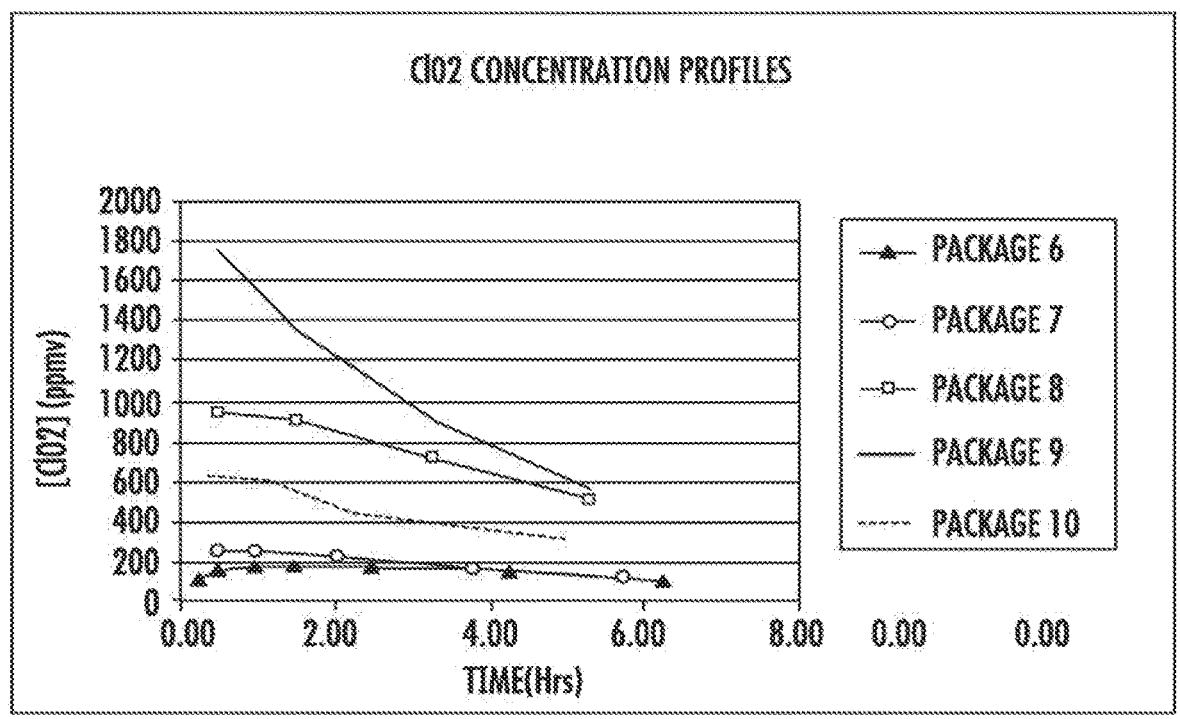
FIG. 7 is a line graph illustrating the chlorine dioxide concentration profile of packages 6-10 over 5-6 hours.

A series of five test packages (Packages 6-10) were prepared with the sachet package test method as set forth above to examine the direct mixing of a sodium chlorite solution with a citric acid solution in the sachet, varying solute concentrations (in each case, the concentration of sodium chlorite was equal to the concentration of citric acid), and headspace volume. To carry out this process, the test method was modified as follows: an empty sachet was positioned inside the test package with an open corner abutting a septum tube. 50 microliters of aqueous sodium chlorite solution and 50 microliters of aqueous citric acid solution were added through the septum tube and into the center of the sachet. The septum port was then capped off and air was introduced via a second septum port. The chlorine dioxide level was monitored over a 7 hour period, as shown in Table 3 and FIG. 7.

TABLE 3

Chlorine Dioxide Headspace Analysis Results of Packages 6-10

| Time After Citric Acid Introduction (hours) | ClO$_2$ Production at 10% aq. reactant conc. | | ClO$_2$ Production at 20% aq. reactant conc. | | ClO$_2$ Production at 15% aq. reactant conc. |
|---|---|---|---|---|---|
| | Package 6 (300 cc Headspace Vol.) | Package 7 (150 cc Headspace Vol.) | Package 8 (300 cc Headspace Vol.) | Package 9 (150 cc Headspace Vol.) | Package 10 (300 cc Headspace Vol.) |
| 0.25 | 122 | — | — | — | — |
| 0.42 | — | — | — | — | 628 |
| 0.50 | 165 | 266 | 947 | 1759 | — |
| 1.00 | 183 | 266 | — | — | — |
| 1.08 | — | — | — | — | 607 |
| 1.50 | 183 | — | 908 | 1364 | — |
| 2.00 | — | 226 | — | — | — |
| 2.25 | — | — | — | — | 445 |
| 2.50 | 176 | — | — | — | — |
| 3.25 | — | — | 711 | 908 | — |
| 3.75 | — | 165 | — | — | — |
| 4.25 | 144 | — | — | — | — |
| 4.92 | — | — | — | — | 319 |
| 5.25 | — | — | 513 | 574 | — |
| 5.75 | — | 122 | — | — | — |
| 6.25 | 97 | — | — | — | — |

The results indicate that chlorine dioxide production is markedly increased when the solute concentration is increased. Also, the headspace concentration was shown to increase as the package headspace volume decreased, indicating that the method would excel for packages having low headspace volume (in contrast with Example 4).

Example 6

Chlorine Dioxide Headspace Analysis Using Citric Acid as Co-Reactant/BI Strip Microbial Assay Testing of antimicrobial effectiveness was carried out by preparing 4 replicates (Packages 11-14) of the 300 cc headspace volume package of Example 5, each with four BI strips inside. Each package was monitored for headspace chlorine dioxide content up to a predefined time point and then flushed with nitrogen gas and opened to remove the BI strips for testing. The results of the headspace and microbial analysis are shown in Tables 4 and 5 below.

Figure 8:
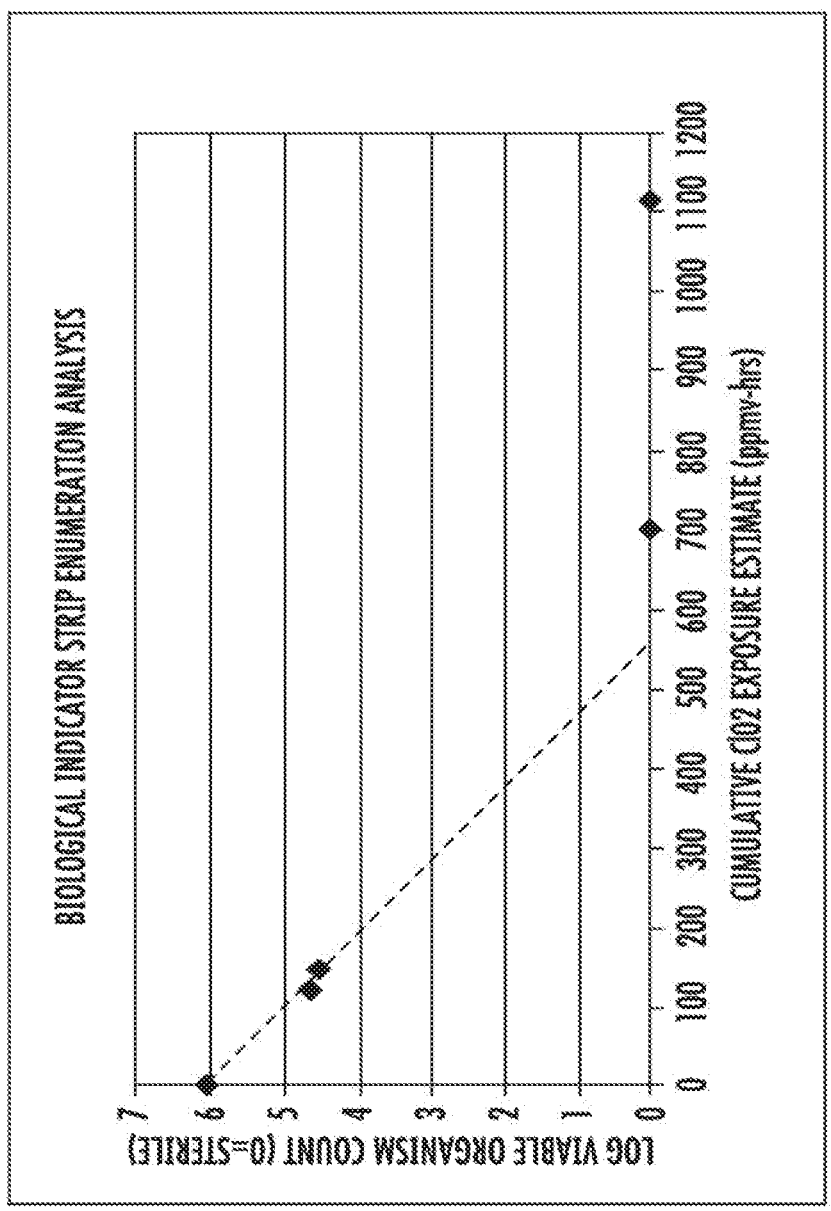
FIG. 8 is a line graph illustrating the log viable organism count versus cumulative chlorine dioxide exposure estimate for Packages 11-14.

Two BI strips were tested for sterility and two were tested for viable organism count alongside an untreated control having a log viable organism count of 6.06. The data demonstrates effectiveness in sterilizing the package interior. FIG. 8 illustrates a plot of enumeration test results versus cumulative exposure estimate, derived from the data in Table 5. The dotted line through the non-zero enumeration values in FIG. 8 suggests that under conditions of this test, there is a minimum exposure requirement of about 550 ppmv-hour for a 6-log reduction in microbial count.

TABLE 4

Chlorine Dioxide Headspace Analysis of Packages 11-14

| Time After Citric Acid Addition (hours) | Package 11 | Package 12 | Package 13 | Package 14 |
|---|---|---|---|---|
| 0.5 | 273[1] | 136 | 370 | 309 |
| 1.0 | | 205[1] | 377 | 320 |
| 2.0 | | | 327[1] | 287 |
| 4.0 | | | | 244[1] |

[1] BI strips removed from package.

TABLE 5

Microbial Assay Results for Packages 11-14

| Measured Parameter | Package 11 | Package 12 | Package 13 | Package 14 |
|---|---|---|---|---|
| Cumulative Exposure Estimate (ppmv-hr) | 120 | 145 | 700 | 1,115 |
| Log Viable Organism Count | 4.67 | 4.56 | n/a | n/a |
| Sterility Assay | Fail | Fail | Pass | Pass |

Example 7

Chlorine Dioxide Headspace Analysis of Packages 15-16

To demonstrate the use of an oxidizing reagent rather than an acid as a co-reactant, and to demonstrate use of different permeable and impermeable film materials, a sachet was constructed from Tyvek® 2FS (available from DuPont Dow Elastomers, Wilmington, Del., United States of America) with a sealant coating, sealed to PL1051 lidding material (available from Sealed Air Corporation, Duncan, S.C., United States of America). The sachets were used in packages (Packages 15, 16) according to the method given in Example 5, except 50 microliters of aqueous 10% sodium chlorite was mixed with 50 microliters of aqueous 15% sodium persulfate in the sachet. The chlorine dioxide level was then monitored over a 5 hour period. The results are shown in Table 6 below.

The results demonstrate a much higher level of chlorine dioxide generation than was achieved in Example 5, which also used 50 microliters of a 10% sodium chlorite solution. The high peak level followed by a relatively rapid rate of decline after 2 hours was consistent with a more rapid and quantitative reaction process to generate chlorine dioxide, running to completion within a shorter time period as compared with acid-chlorite chemistry.

TABLE 6

Chlorine Dioxide Headspace Analysis Results of Packages 15-16

| Time After Sodium Persulfate Addition (hrs) | Package 15 (300 cc Air Headspace) | Package 16 (150 cc Air Headspace) |
|---|---|---|
| 0.50 | 926 | 1508 |
| 0.70 | — | 1458 |
| 2.00 | 1052 | 1199 |
| 4.75 | 273 | 316 |

Example 8

Chlorine Dioxide Headspace Analysis of Dual-Lid Packages 17-20

Dual-lid packages 17-20 were prepared according to Table 7 below to demonstrate the conditions of Example 7 by replacing the sachet inside a pouch with a dual-lid thermoformed package constructed according to the Dual Lid Package Test Method above.

TABLE 7

Preparation of Packages 17-20

| Package No. | Reagent Conc. (wt %) | Reagent Vol. (ul/package) | Package vol. (cc) | Package contents |
|---|---|---|---|---|
| 17 | 15 | 16.7 | 100 | none |
| 18 | 15 | 16.7 | 150 | none |
| 19 | 15 | 33.5 | 100 | none |
| 20 | 15 | 33.5 | 150 | none |

3 repeats of each package were prepared, and the chlorine dioxide content at 1 hour was tested. The results are shown in Table 8 and demonstrate that the dual-lid format is highly effective at generating levels of chlorine dioxide that are in the several thousand ppm range. The results also demonstrate the ability to control the level of chlorine dioxide by varying package and reagent volumes.

TABLE 8

Chlorine Dioxide Content for Packages 17-20

| Package No. | Trial 1 | Trial 2 | Trial 3 | Average |
|---|---|---|---|---|
| 17 | 1831 | 1508 | 1364 | 1568 |
| 18 | 847 | 1058 | 854 | 920 |
| 19 | 4093 | 3554 | 3411 | 3686 |
| 20 | 2405 | 2513 | 2585 | 2501 |

Example 9

Chlorine Dioxide Content Measurements of Packages 21-24

The procedure of Example 8 was followed using a reduced concentration of reagent, as set forth in Table 9 below.

TABLE 9

Packages 21-24 Configurations

| Package No. | Reagent Conc. (wt %) | Reagent Vol. (ul/package) | Package Vol. (cc) | Package contents |
|---|---|---|---|---|
| 21 | 10 | 16.7 | 100 | none |
| 22 | 10 | 16.7 | 150 | none |
| 23 | 10 | 33.5 | 100 | none |
| 24 | 10 | 33.5 | 150 | none |

3 repeats of each condition were prepared and the chlorine dioxide content at one hour was tested. The results are shown in Table 10 below. Taken together with Example 8, the data demonstrates the ability to control the level of chlorine dioxide by varying the reagent concentration, as well as the package volume and the reagent volume.

TABLE 10

Chlorine Dioxide Content of Packages 21-24

| Package No. | Trial 1 | Trial 2 | Trial 3 | Avg. |
|---|---|---|---|---|
| 21 | 607 | 531 | — | 569 |
| 22 | 420 | 355 | 424 | 400 |
| 23 | 1903 | 1723 | 1580 | 1735 |
| 24 | 1228 | 1145 | 976 | 1116 |

Example 10

Chlorine Dioxide/BI Strip Testing of Packages 25-28

The method used in Example 9 was followed with the same conditions except the addition of a stainless steel surgical saw blade and a pair of BI strips was added to packages 25-28, as set forth in Table 11.

TABLE 11

Configuration of Packages 25-28

| Package No. | Reagent Conc. (wt %) | Reagent Vol. (uL/pkg) | Package Vol. (cc) | Package Contents |
|---|---|---|---|---|
| 25 | 10 | 16.7 | 100 | Saw blade/2 BI strips |
| 26 | 10 | 16.7 | 150 | Saw blade/2 BI strips |
| 27 | 10 | 33.5 | 100 | Saw blade/2 BI strips |
| 28 | 10 | 33.5 | 150 | Saw blade/2 BI strips |

Two trials of each package were prepared, with the first tested at 1 hour and the second tested at 4 hours. Testing for each package included headspace chlorine dioxide analysis, enumeration testing of one BI strip, and sterility testing of the second BI strip. The results are shown in Table 11 below. The chlorine dioxide levels at 1 hour can be compared with the results from Example 9 (Table 10), showing that a significant reduction resulted when the saw blade and BI strips were present in the package, indicating adsorption by the package contents. The test also demonstrated the efficacy of the packages as a sterilization method. It was interesting to note that the 1 hour and 4 hour samples for Package 26 yielded no measureable chlorine dioxide in the headspace, yet the BI strips from the 4 hour sample were sterile and there was about a 4-log reduction in viable organisms after 1 hour, indicating that a transient level of chlorine dioxide, fully taken up by the package contents in less than 1 hour, was still sufficient to effect sterilization.

TABLE 11

Chlorine Dioxide/BI Strip Testing of Packages 25-28

| | 1 Hour | | | 4 Hours | | |
|---|---|---|---|---|---|---|
| Package No. | [$ClO_2$] (ppmv) | Enum. (log count) | Sterile (yes/no) | [$ClO_2$] (ppmv) | Enum. (log count) | Sterile (yes/no) |
| 25 | 219 | 2.70 | No | 54 | — | Yes |
| 26 | <10 | 2.08 | No | <10 | — | Yes |
| 27 | 661 | — | Yes | 244 | — | Yes |
| 28 | 600 | — | Yes | 251 | — | Yes |

What is claimed is:

1. A method of sterilizing, sanitizing, or disinfecting a product, said method comprising:
   a. sealing the product into an interior of a package comprising:
      the interior; and
      at least one dual-layer wall comprising:
      i. an inner permeable layer,
      ii. an outer impermeable layer, and
      iii. an intersticial space positioned between the inner and outer layers, wherein the intersticial space comprises a reactant solution having a reactant and a co-reactant that combine to produce a gas that at least one of sterilizes, sanitizes and disinfects, wherein the reactant solution having a 1-40 weight percent aqueous chlorite or chlorate salt solution and a pH of 8-13 prior to addition to the package;
   b. waiting a desired amount of time to effect sterilization, sanitation, or disinfection; and
   c. unsealing the package to access the product.

2. The method of claim 1, wherein said product is a medical product.

3. The method of claim 1, wherein the amount of reactant solution is about 0.1 to 10 microliters per $cm^2$ of dual layer wall.

4. The method of claim 1, wherein the reactant solution is introduced between the inner and outer layers prior to sealing the package.

5. The method of claim 4, wherein the reactant solution is delivered as the inner and outer layers are moving into the sealing zone for sealing the package on an automated packaging machine.

6. The method of claim 1, wherein the gas comprises at least one of chlorine dioxide, dichlorine monoxide and ozone.

7. The method of claim 6, wherein the peak concentration of the gas inside the package is between 10 ppmv and 10,000 ppmv.

8. The method of claim 1, wherein a gas sensor is used outside the package during sterilization to detect leakage of gas from the package.

* * * * *